United States Patent [19]

Palmer

[11] Patent Number: 5,210,272
[45] Date of Patent: May 11, 1993

[54] PROCESS FOR FORMING A FLUOROMETHYL KETONE

[75] Inventor: James T. Palmer, San Ramon, Calif.

[73] Assignee: Prototek, Inc., Dublin, Calif.

[21] Appl. No.: 744,922

[22] Filed: Aug. 14, 1991

Related U.S. Application Data

[62] Division of Ser. No. 481,995, Feb. 16, 1990, Pat. No. 5,101,068.

[51] Int. Cl.$^5$ .................. C07C 315/04; C07C 45/41
[52] U.S. Cl. ................................ 560/13; 530/330; 530/331; 530/335; 560/37; 560/51; 560/169; 560/170; 560/174; 560/192; 568/319; 568/355; 568/397
[58] Field of Search ............... 560/13, 37, 51, 169, 560/170, 174; 568/319, 355, 397

[56] References Cited

U.S. PATENT DOCUMENTS 4,518,528  5/1985  Rasnick ........................ 530/329

OTHER PUBLICATIONS

Rozen, S. et al., *Tetrahedron Letters*, 41:1111–1153, (1985).
Brooks, D. W. et al., *Angew. Chem. Int. Ed. Eng.*, 18:72–74, (1979).
Mansour, T. S., *Synth. Commun.*, 19 (Nos. 3 & 4): 659–665, (1989).

*Primary Examiner*—José G. Dees
*Assistant Examiner*—Vera C. Clarke
*Attorney, Agent, or Firm*—Woodard, Emhardt, Naughton, Moriarty & McNett

[57] ABSTRACT

The preparation of magnesium benzyl fluoromalonate and other equivalent materials, the synthetic equivalents of the —CH$_2$F moiety, is described. Reaction between these reagents and the in situ-formed imidazolides of various carboxylic acids gives beta-keto-alpha-fluoroesters, which upon hydrogenation and spontaneous decarboxylation yields fluoromethyl ketones in excellent yields. The overall transformation from RCOOH to RCOCH$_2$F is thus illustrated.

5 Claims, No Drawings

PROCESS FOR FORMING A FLUOROMETHYL KETONE

This application is a division of application Ser. No. 07/481,995 filed, Feb. 16, 1990, now U.S. Pat. No. 5,101,068.

BACKGROUND OF THE INVENTION

1. Field of the Invention

This invention is in the field of synthetic chemistry. More particularly, it relates to a new method and to new reagents for introducing the fluoromethyl group, —$CH_2F$, onto carbonyl carbons in organic structures. These new reagents are most specifically embodied as magnesium benzylfluoromalonates.

2. Description of Background Information

Fluorination of organic compounds poses several difficulties. For one, the classic methods of fluorination typically employ harsh conditions which can be destructive or disruptive to many organic structures. Similarly, the reagents employed in many fluorinations are often hazardous and difficult to work with safely. This can render scale-up of reactions problematic. In addition, the unique electronic properties of the fluorine atom and its effects on neighboring groups make it difficult to analogize fluorination reactions with other, seemingly similar, reactions such as chlorinations.

Nonetheless, selective monofluorination of organic compounds has become an area of increasingly great interest in recent years (Haas, A.; Lieb, M. *Chimia*, (1985), 39, 134; Rozen, S.; Filler, R.; *Tetrahedron*, (1985), 41, 1111; Purrington, S.T.; Kagen, B.S.; Patrick, T.B. *Chem. Rev.*, (1986), 86, 997). In light of the vast potential of fluorinated compounds of medicinal and biological interest (welch, J.T. *Tetrahedron*, (1987), 43, 3123), new methods for introduction of a single fluorine atom into various species are in high demand. Several new methods have been recently published, including the use of dilute elemental fluorine, (Purrington, S.T.; Lazaridis, N.V.; Bumgardner, C.L. *Tetrahedron Lett.*, (1986) 27, 2715. Purrington, S.T.; Bumgardner, C.L.; Laziridis, N.V.; Singh, P. *J. Org. Chem.*, (1987), 52, 4307)) and N-fluorinated species (Umemoto, T.; Tomita, K. *Tetrahedron Lett.*, (1986), 27, 3171. Umemoto, T.; Kawada, K.; Tomita K. *Tetrahedron Lett.*, (1986), 27, 4465. Lang, R.W.; Differding, E. *Tetrahedron Lett.*, (1988), 29, 6087) as sources of electrophilic fluorine.

In many cases, particularly as related to compounds of biological interest, it is necessary to have a method for introducing fluoromethyl groups into stereospecific organic molecules. In the area of peptide analog synthesis there is a need for an extremely mild method for transforming alpha-amino acids to the corresponding fluoromethyl ketones without disrupting the alpha—amino acid's stereochemistry. The need to maintain stereochemical integrity in the amino acid makes this transformation particularly difficult. A modified DakinWest reaction (Rasnick, D. *Analytical Biochem*, (1985), 149: 461) that has been used to effect this type of transformation is limited not only by the necessary loss of stereochemistry at the amino acid residue as a result of the proposed mechanism (Wiley, R.H.; Borum. O.H. *Org. Syn.*, (1963), *Coll. Vol.* 4:5), but also by the sterics of the alkyl residue in question.

The present invention provides an extremely mild stereoselective method for introducing fluoromethyl groups into organic compounds. It employs a reactive metal salt of an aryl or aralkyl fluoromalonate. In 1979, Brooks and Masamune (Brooks, D.W.; Lu. L.; Masamune, S. *Angew. Chem. Int. Ed. Eng.*, (1979), 18: 72) reported the use of magnesium malonates to introduce methyl and alkyl-substituted methyl groups into organic structures. The reaction of the carboxyl group with the malonate and the placement of the methyl or alkyl-substituted methyl on the carboxyl carbonyl is shown in Equation 1.

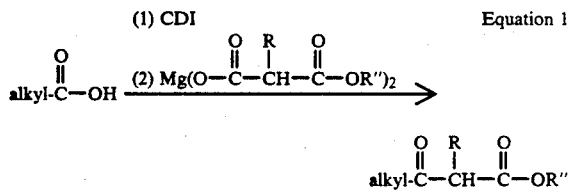

Equation 1

Wherein
  CDI = carbonyl 1,1'-diimidazole
  R" = alkyl, aryl etc.
  R = hydrogen or alkyl The use of this methodology to introduce these simple alkyl groups is well documented. (See, e.g., Bodurow, C.C., et al. *Tetrahedron Lett.*, (1989), 30, 2321. Mansour, T.S. *Synth. Commun.*, (1989), 659. Hashiguchi, S.; Natsugari, H.; Ochiai, M. *J. Chem. Soc. Perkin Trans. I.*, (1988), 2345. Maibaum, J.; Rich, D.H. *J. Org. Chem.*, (1988), 53, 869. Ha, D.C.; Hart, D.J. *J. Antibiotics*, (1987), 40, 309. Liu, L.; Tanke, R.S.; Miller, M.J. *J. Org. Chem.* (1986), 51, 5332. Nagahara, T.; Kametani, T. *Heterocycles*, (1987), 25, 729. Brooks, D.W.; Palmer. J.T. *Tetrahedron Lett.*, (1983), 24, 3059. Pollet, P.L. *J. Chem. Ed.* (1983), 60, 244. Kametani, T.; Fukumoto, K.; Ihara, M. *Heterocycles*, (1982), 17, 463. Melillo, D.G.; Liu, T.; Ryan, K.; Sletzinger, M.; Shinkai, I. *Tetrahedron Lett.*, (1981), 22, 913. Salzmann, T.N.; Ratcliffe, R.W.; Christensen, B.G.; Bouffard, F.A. *J. Am. Chem. Soc.* (1980), 102, 6161). However, this chemistry has not been demonstrated to be applicable with alpha substituents other than alkyl groups or hydrogen. Moreover, the reagents needed to carry out fluoromethylations with this type of chemistry have not been available.

STATEMENT OF THE INVENTION

A new method for introducing fluoromethyl groups into organic structures has now been developed. The method finds special application to the conversion of carboxyl groups to fluoromethyl ketone groups. It is characterized as being mild enough to permit the attachment of the fluoromethyl group to the carboxyl carbonyl without disrupting the stereochemistry of the organic structure in which it is contained. The methodology involves the use of magnesium fluoromalonates of Formula 2.

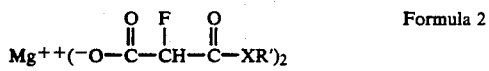

Formula 2 wherein X is —O— or —S—, and

R' is a hydrogenolytically cleavable group such as a polyhaloalkyl, silylalkyl, or aralkyl group. These magnesium fluoromalonate synthons are one aspect of this invention.

In another aspect, this invention provides a method for introducing fluoromethyl groups into organic compounds. This method is a multistep process which in one embodiment involves forming a beta-keto-alpha-fluoro-ester of a carboxylic acid by a. converting the carboxyl group of the carboxylic acid to the corresponding imidazolide, and
b. reacting the imidazolide with a magnesium fluoromalonate of Formula 2.

In yet an additional aspect, this invention provides the further process wherein the beta-keto-alpha-fluoroester so formed is hydrogenated thereby causing its decarboxylation and formation of the corresponding fluoromethyl ketone.

DESCRIPTION OF PREFERRED EMBODIMENTS

The Metal Fluoromalonates

The metal fluoromalonates which this invention involves have the structure set out as Formula 2

$$Mg^{++}(^-O-\underset{\underset{O}{\|}}{C}-\underset{\underset{F}{|}}{CH}-\underset{\underset{O}{\|}}{C}-XR')_2 \quad \text{Formula 2}$$

In Formula 2, X is an oxygen linkage (—O—) or sulfur linkage (—S—) with the oxygen linkage being preferred.

In Formula 2, R' is a hydrogenolytically cleavable group. This is a group which can be removed by the action of molecular hydrogen and a hydrogenation catalyst under moderate conditions. Most commonly this is an aralkyl group especially a benzyl or substituted benzyl. Aralkyls can include a 6 to about 10 carbon atom aryl group (i.e. phenyl) or dicyclic (i.e. naphthyl) attached to a bridging methylene. These aralkyl groups can be substituted. Typical substituents include lower alkyl groups, halos, nitros and the like. As used here, the term "alkyl" typically refers to "lower alkyl groups" which are defined to be alkyls having from 1 to 4 carbon atoms. Preferably, the substituents, if any, are of a nature and position on the aralkyl group to increase the groups electronegativity and thus its lability in the subsequent hydrogenative cleavage reactions. For example, an electronegative group such as a nitro group located at the 4 or para position of a benzyl can increase the ease with which this benzyl is later displaced. In addition, R' can be a polyhaloalkyl, particularly a 1 or 2 carbon alkyl containing 2 or more chlorines or fluorines. Such R' moieties include, a —CCl$_3$, —CF$_3$, —CCl$_2$—CH$_3$, and the like. Other groups useful as R' include silyl alkyls, such as silyl methyl or silyl ethyl, and other groups removable by the action of molecular hydrogen and a hydrogenation catalyst.

Of the magnesium fluoromalonates described by Formula 2 special preference is given to materials wherein X is —O— and R' is benzyl or para-nitrobenzyl.

Preparation of the Fluoromalonates

The magnesium fluoromalonates Of this invention can be generated by the sequence of reactions shown in Scheme 3. In Scheme 3 the R' group is depicted as benzyl and —X— is —O—. As will be appreciated, the same general scheme is applicable to other materials within the scope of this invention as well.

Scheme 3

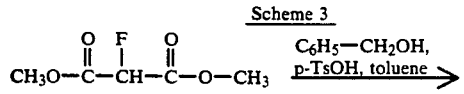

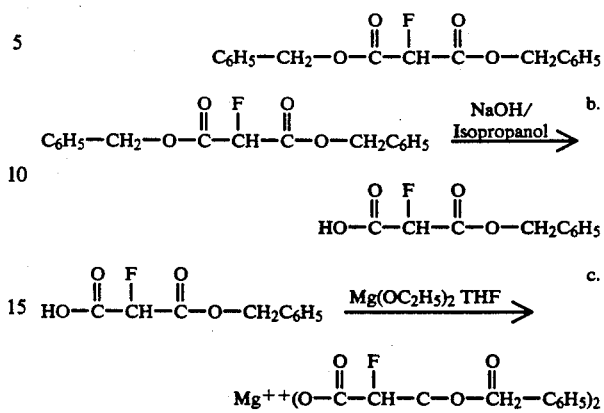

The starting fluoromalonate of Scheme 3 can be made from hexafluoropropane which is reacted with ammonia using the method of Ishikawa et al. *J. Fluorine Chem.* (1984), 24, 203–212 to 2,3,3,3-tetrafluoropropionitrile. This product is then treated with an alcohol solution of a strong base, for example an alkali metal alkoxide, to yield the dialkyl fluoromalonate starting material. In the first step of Scheme 3 (step a), a dimethyl fluoromalonate is subjected to an ester exchange with the appropriate R'-OH alcohol in the presence of a strong acid catalyst. In step b of Scheme 3 the alcohol is shown as benzyl alcohol, but other equivalent alcohols corresponding to the R' group in Formula 2 can be used. Similarly, other strong acid catalysts can be used in place of the p-toluene sulfonic acid catalyst shown in step a. This reaction takes from 1 to 10 hours and requires elevated temperature such as from 50° to 110° C. to complete. This reaction is run under 10–29 inches of vacuum so as to distill methanol as if is formed and thus avoid side reactions with the methanol which is liberated. Other reaction conditions include a lower alkanol (isopropanol) solvent and a temperature of 40° to 50° C. (especially 45° C.) for 0.5 to 3 hours (especially 1 to 1.5 hours) with careful control of pH to the acid side such as to between about pH 1 to 5, and especially about 2, during workup.

The product of step a is typically a crystalline solid which may be readily isolated and purified. Such procedures can be carried out by crystallization or the like.

In step b, one of the two R' ester groups of the R' fluoromalonate is saponified using the general methods of Breslow, D.S., et al. *J. Am. Chem. Soc.* (1944). 66, 1286. This reaction is somewhat difficult because the transesterification reaction (by reaction with unhindered alcohol solvents) is much faster than the saponification. Using 1M alkali metal hydroxide in lower (C$_1$-C$_4$) aliphatic alcohol, one of the two aryl groups is replaced on average to give the mono R'-fluoromalonate. Typically about 1-1.2 equivalents of base are used. The mono-R' fluoromalonate is then converted to a magnesium salt, typically by reaction with a basic organic-soluble magnesium salt such as Mg alkoxide (methoxide, ethoxide or isopropoxide or the like). It has been observed that this reaction needs to be carefully monitored to prevent side reactions such as the formation of an alcohol by reaction of the metal alkoxide with acid and subsequent reaction of this alcohol in an ester exchange with the mono R'-fluoromalonate. This reaction can give rise to a dialkyl fluoromalonate which will not include the required R' group. This side reaction can give rise to an inseparable mixture of products in subsequent reactions, as well. This problem can be minimized by using about the ideal stoichiometric ratio of the fluoromalonate to metal alkoxide (two moles of fluoromalonate per mole of alkoxide) and also by removing the desired product promptly from the reaction mixture such as by precipitation after not more than about 2 to 3 hours reaction at room temperature.

The quality of the final product is affected by the purity of the magnesium reagent. Strict control of the purity and use of the magnesium reagent will minimize the likelihood that impurities might surface later. For example, it was noted that when benzyl fluoromalonic acid was permitted to react with magnesium ethoxide for longer than 2 or 3 hours, or was allowed to stand in the THF solution for any length of time beyond this, ethanol produced as the result of reaction between the acid and magnesium ethoxide. This ethanol reacted in an ester exchange manner with the magnesium benzyl fluoromalonate, giving a product contaminated with magnesium ethyl fluoromalonate. When used in the C-acylation step, the result was an inseparable mixture of beta-keto benzyl ester and beta-keto ethyl esters. Another difficulty was the appearance of fluoromalonic acid (and subsequently its magnesium salt) in some batches of magnesium benzyl fluoromalonate. In all cases, however, the optimum quality of magnesium benzyl fluoromalonate was obtainable simply by maintaining strict pH control during isolation of benzyl fluoromalonic acid, and by precipitating magnesium benzyl fluoromalonate immediately from its filtered THF solution with hexane.

The Fluoromethnylation Process

The fluoromethylation process which makes up another aspect of this invention involves several reactions. This process is carried out on a carboxylic acid group-containing organic compound and has as its ultimate objective the replacement of the hydroxyl present in the carboxylic acid group with a fluoromethyl (—CH$_2$F). This process is shown generally in Reaction Scheme 4.

Reaction Scheme 4

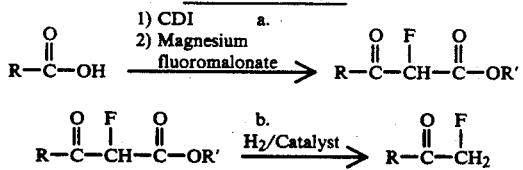

The choice of carboxylic acid group containing compound

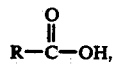

can be made broadly and without limitation. Typical acids can include, for example, simple unsubstituted lower and intermediate length (2 to 10 carbon) aliphatic acids such as acetic acid, propionic acid, 2-ethylhexanoic acid and the like; longer chain (10 to 20 carbon) aliphatic acids such as the fatty acids - caproic acid, stearic acid, linoleic acid, oleic acid and the like; cyclic aliphatic acids such as cyclohexanoic acid, hydnocarpic acid, camphoric acid, abietic acid, agathic acid and the like; aromatic acids such as benzoic acid, naphthenic acid and the like; and acids such as the amino acids which are characterized by containing labile or reactive groups which are likely to be disturbed or displaced by prior art modes of fluoromethylation.

While this expansive list is important to illustrate the broad scope of applicability of the present invention, it will be recognized that the most valuable applications of the present process are typically with sensitive acids which have a particular stereochemistry that needs to be retained. Biologically important acids such as the amino acids, sugars, nucleosides, etc. are among these preferred acids.

In the first step of the fluoromethylation process the carboxyl functionality of the selected carboxylic acid is reacted to yield the corresponding imidazolide. This reaction is the first reaction shown in Reaction Scheme 4 (step a1) and is conveniently carried out by reacting the carboxylic acid group containing compound with carbonyl 1,1'-diimidazole (CDI). This reaction can be carried out simply by mixing the carboxylic acid with about 1 stoichiometric equivalent of CDI for about 1 hour at room temperature. If desired, lower temperatures such as down to 0° C., can be used with appropriate adjustments in reaction times into the range of from 1 to 4 hours. The reaction is typically carried out in an inert liquid organic reaction phase such as THF, DMF, or other similar materials. THF is the preferred reaction medium.

The second step of Reaction Scheme 4 (step a2) is carried out directly. The imidazolide intermediate does not need to be isolated but rather can be reacted in situ with the magnesium fluoromalonate. Since one mole of the magnesium fluoromalonate provides two equivalents of the fluoromalonate ion, the amount of magnesium fluoromalonate is preferably controlled so that from about 1 to about 2, and especially from about 1 to about 1.5, equivalents of fluoromalonate ion is added per equivalent of imidazolide. This reaction is carried out in an inert solvent such as DMF or THF and at room temperature (20° to 25° C.) and is complete in 6 to 12 hours. More general reaction conditions are temperatures of from 0° to 50° C. with times of from 1 to 30 hours being used. The best conditions for this reaction have been to use THF solvent, an inert atmosphere and 25° C. for 6 hours.

At the completion of this reaction, the reaction medium is subject to aqueous workup. The desired fluoromalonate adduct is then recovered, e.g., by extraction into a polar solvent such as ethyl acetate or toluene with toluene being preferred.

In the third step of Reaction Scheme 4 (step b.), the fluoromalonate adduct is subjected to hydrogenolytic cleavage using hydrogen gas and a suitable hydrogenation catalyst such as nickel, platinum on a support, palladium on a support, or the like. This can be carried out with the adduct dissolved in a liquid reaction medium such as toluene, ethyl acetate or a similar ester, or an alcohol such as ethanol or methanol. The amount of catalyst is not critical, with, say, 1 to 20% by weight of total catalyst plus support (based in the weight of fluoromalonate being treated) being typical. A molar excess (1 or more equivalents based on the equivalents of fluoromalonate adduct being treated) of H$_2$ is used. Temperatures can range from low room temperature (10° C.) to 50° C. Higher and lower temperatures can be used, if desired and if facilitated by the catalyst employed. At room temperature and using a palladium catalyst, the reaction is substantially complete in about 16 hours so that with the various catalysts and temperatures called for, the time needed can range between about 1 and about 72 hours at $H_2$ pressures of from about 1 or 2 psig to about 200 psig or higher.

This hydrogenation will cleave the fluoromalonate group and generate the ultimately desired fluoromethyl ketone compounds which make up another aspect of this invention.

Depending upon the exact nature of the acid employed as starting material and whether or not it contained active sites which required blocking prior to conversion of the carboxyl group to the fluoroketone it may be called for to carry out various deblocking steps and the like. For example, there can be deprotection of alpha-blocking groups, followed by mixed anhydride condensation with the appropriate amino acid sequence. This can afford the appropriate peptide fluoromethyl ketones, which can then be used as protease inhibitors.

In the description of this chemical process, ranges of conditions have been provided. It will be appreciated that harsher conditions (e.g., higher temperatures, higher $H_2$ pressures) might be employed to speed the reactions to completion. However, these harsher conditions may have the undesirable effects of leading to by-products and/or racemizing optical centers, and the like. The process of this invention generally is employed to minimize these undesirable effects. As such, it is often preferred to use less efficient but milder conditions when there is a choice.

These choices of milder conditions are consistent with the use of R' groups in the fluoromalonates which are easily removed with the $H_2$/catalyst reaction systems. If one were to substitute an alkyl or an aryl for the aralkyls, these would be less labile and would require harsh base cleavage conditions or the like to remove. These conditions would also lead to racemization of the final product.

Uses of the Products

The fluoromethyl ketones of amino acids which are produced by this invention and the fluoromethyl ketone derivatives of peptides which can be formed from them can be used as enzyme inhibitors. Representative materials are shown in U.S. Pat. No. 4,518,528, together with their use as protease inhibitors. Because of its utility, one particular fluoromethyl ketone material which can be made by the present invention bears special mention:

Z-Phe-Ala—$CH_2F$, wherein Z is benzyloxy carbonyl; The present process is the first known to achieve this material as well as the other materials shown in the '528 patent in optically pure form, either D or L.

EXAMPLES

This invention will be further illustrated by the following examples. These are presented to give experimental details of typical embodiments of this invention and are not to be construed as limiting this invention's scope.

Experimental

General: Melting points were recorded on a Mel-Temp II. Optical rotations were recorded on a Perkin-Elmer 241 MC (Marion Laboratories, Inc., Kansas City, MO). Infrared spectra were recorded on a Perkin-Elmer 1600. IR data are reported as $cm^{-1}$. $^1H$ and $^{19}F$ NMR spectra were recorded on an IBM-Bruker FT-100: $^1H$ NMR data are reported as delta values in parts per million relative to internal tetramethylsilane; $^{19}F$ NMR data are reported as delta values in parts per million relative to external $CFCl_3$. THF was distilled from sodium benzophenone ketyl. The following abbreviations are used: s, singlet; d, doublet; t, triplet; q, quartet; br, broad. An asterisk (*) implies that a signal is obscured or buried under another resonance. All other solvents and commercially available reagents were used without further purification. Unless otherwise indicated, all reactions were performed under an inert atmosphere of nitrogen.

EXAMPLES

Dibenzyl Fluoromalonate. A 3-neck, 5-L round-bottom flask equipped with a vacuum distillation head, a thermometer, and a magnetic stir bar was charged with dimethyl fluoromalonate (339 g assayed at 83% purity by VPC, 1.88 mol), benzyl alcohol (935 mL, 9.04 mol), toluene (846 mL), and p-toluenesulfonic acid monohydrate (21.5 g, 0.113 mol). The mixture was heated under vacuum (10-15 inches of Hg) until all of the toluene had distilled, then at 28-29 inches of Hg (water aspirator vacuum), the reaction temperature being maintained at 100° to 115° C. The progress of the reaction was monitored by $^{19}F$ NMR. After a total of 7 hours, the heat was removed, and the mixture was allowed to cool, with continued stirring. When the temperature had lowered to 75° C., isopropanol (450 mL) was added. When the temperature had lowered to 55° C., hexane (1 L) was added. The product crystallized out and the mixture was placed in the freezer overnight. The product was filtered, washed with hexane (2xl L), sucked dry, and dried overnight in vacuo. The yield was 452 g (96% pure by weight). A second crop of 29 g was obtained from the combined filtrates and washings, for a total yield of 81%.

$^1H$ NMR ($CDCl_3$): 7.32 (10H, s, aromatic); 5.61,5.07 (1H, d, J=47 Hz, CHF); 5.23 (4H, s, $PhCH_2$). $^{19}F$ NMR ($CDCl_3$) -194.93 (1F, d, J=47 Hz). M.p. 43°-45° C.

EXAMPLE 2

Benzyl Fluoromalonic Acid. Dibenzyl fluoromalonate (87.2 g, 289 mmol) was suspended in isopropanol (480 mL) in a 2-L Erlenmeyer flask equipped with a magnetic stir bar and thermometer. The mixture was heated, with stirring, to 45° C., by which time the solids had dissolved. Over a 1 hour period, 1M aqueous NaOH (303 mL, 1.05 eq.) was added via a metered addition funnel. After an additional 10 minutes, the solution was concentrated in vacuo to a volume of approximately 200 mL. Water was added to a total volume of 300 mL. The pH of the solution was adjusted to 8.6 using saturated aqueous $NaHCO_3$. The mixture was washed with $CH_2Cl_2$ (2×100 mL) to remove benzyl alcohol. The pH of the aqueous layer was adjusted to 2.0 with 6M HCl. The mixture was extracted with ethyl acetate (200 mL). The pH of the aqueous layer was adjusted to 2.0 with 1M HCl, and a second 200 mL ethyl acetate extraction was performed. The combined extracts were washed with saturated aqueous NaCl (150 mL), dried over $MgSO_4$, filtered, and evaporated to dryness, the rotary evaporator bath being 35° C. or less. The oily residue was triturated with hexane (300 mL) overnight. The solids were broken up, filtered, and pumped dry, yielding 44.7 g (73%) of benzyl fluoromalonic acid.

In subsequent experiments best results were obtained by use of diisopropyl ether (instead of ethyl acetate) as the extraction solvent following the benzyl fluoromalonic acid synthesis. The quality of the magnesium salt that was subsequently formed was best when the starting material had been derived in this manner.

1H NMR (CDCl$_3$) 9.4–8.9 (1H, br.s, COOH); 7.37 (5H, s, aromatic); 5.61, 5.18 (1H, d, J=47 Hz, CHF); 5.30 (2H, s, PhCH$_2$). $^{19}$F NMR (CDCl$_3$) -195.14 (1F, d, J=47 Hz).

EXAMPLE 3

Magnesium Benzyl Fluoromalonate. Benzyl fluoromalonic acid (22.3 g, 105.2 mmol) was dissolved in THF (150 mL). Magnesium ethoxide (6.14 g, 52.6 mmol, 98%, Aldrich) was added. The mixture was stirred vigorously under N$_2$ for 2 hours, and filtered through a pad of Celite, the solids being washed with THF (2×20 mL). The clear solution was poured carefully into hexane (1.1 L) with vigorous stirring. The white precipitate was immediately filtered, washed with hexane (2×50 mL), and the filter cake was pumped dry overnight. The product was broken up to a fine white powder. Yield=18.7 g (80%)

$^1$H NMR (CDCl$_3$): 7.25 (5H, s, aromatic); 5.33, 4.81 (1H, d, J=47 Hz, CHF); 5.10 (2H, s, PhCH$_2$). $^{19}$F NMR (CDCl$_3$): 187.3, 187.8 (1F, d, J=47 Hz).

EXAMPLE 4

General Procedure for beta-keto-alpha-fluoroester Synthesis. To a solution of carboxylic acid (such as the materials identified in Table 5 as 1a-j) in THF (0.2M) is added carbonyl 1,1-diimidazole (1.0 equivalents). The solution is stirred for 1 hour at room temperature under N$_2$. Magnesium benzyl fluoromalonate (1.0 equivalents) is added. The mixture is stirred overnight at room temperature (longer reaction times being needed for valine). 0.5 M HCl is added. The product is extracted twice with ethyl acetate, the combined extracts are washed with saturated aqueous NaHCO$_3$, brine, dried over MgSO$_4$, filtered, and evaporated to dryness, giving the products identified in Table 5 as 2a-j.

EXAMPLE 5

Specific Procedure: (4S)-4-tert-butoxycarbonylamino-2-fluoro-6-methyl-3-oxoheptanoic acid, benzyl ester. Boc-leucine monohydrate (3.00 g, 12.05 mmol) was azeotropically dried by coevaporation of a solution of the acid in 1:1 toluene/ethyl acetate (100 mL). The oily residue was dissolved in THF (60 mL). CDI (1.95 g, 12.05 mmol) was added. The mixture was stirred at room temperature for 1 hour under N$_2$, whereupon magnesium benzyl fluoromalonate (MBFM) (5.38 g, 12.05 mmol) was added. The mixture was stirred at room temperature overnight. 0.5 M HCl (120 mL) was added. The product was extracted with ethyl acetate (2×50 mL), the combined extracts were washed with saturated aqueous NaHCO$_3$ (80 mL), brine (40 mL), dried over MgSO$_4$, filtered, and evaporated to dryness, to give a pale yellow oil, BocLeuCHFCOOBzl compound in Table 5 (3.95 g, 86%).

EXAMPLE 6–14

The procedure of Examples 4 and 5 was repeated 9 times each with different amino acid-based starting materials. The details of each of these examples are given in Table 5.

$^1$H NMR, $^{19}$F NMR, and IR data are shown in Table 6 for compounds 2a-j of Table 5. In several instances, the spectra are less than totally clear owing to the presence of two isomers, epimeric at the CH-F bond, not always in equal proportion. The fluorine spectra readily identify this. In particular, the proline entry (2f) exhibited substantial long-range coupling between the fluorine and the chiral methine, leading to a complicated spectrum containing two distinct doublets of doublets.

TABLE 5

$$R\overset{O}{-}OH \xrightarrow[\text{2) MBFM}]{\text{1) CDI}} R\overset{O}{-}\underset{F}{-}\overset{O}{-}OBzl \xrightarrow{H_2/Pd} R\overset{O}{-}F$$

| ENTRY | | | | YIELD (2a-j/3a-j) |
|---|---|---|---|---|
| 1a | Boc—AlaOH | 2a Boc—AlaCHFCOOBzl | 3a Boc—AlaCH$_2$F | 93%/80% |
| 1b | Boc—PheOH | 2b Boc—PheCHFCOOBzl | 3b Boc—PheCH$_2$F | 93%/73% |
| 1c | Boc—ValOH | 2c Boc—ValCHFCOOBzl | 3c Boc—ValCH$_2$F | 69%/97% |
| 1d | Fmoc—LysOH<br>\|<br>Boc | 2d Fmoc—LysCHFCOOBzl<br>\|<br>Boc | 3d Fmoc—LysCH$_2$F<br>\|<br>Boc | 82%/18%$^a$ |
| 1e | Boc—ArgOH<br>\|<br>Mtr | 2e Boc—ArgCHFCOOBzl<br>\|<br>Mtr | 3e Boc—ArgCH$_2$F<br>\|<br>Mtr | 53%/33%$^a$ |
| 1f | Boc—ProOH | 2f Boc—ProCHFCOOBzl | 3f Boc—ProCH$_2$F | 52%/90% |
| 1g | Boc—AspOH<br>\\<br>(OBzl) | 2g Boc—AspCHFCOOBzl<br>\\<br>(OBzl) | 3g 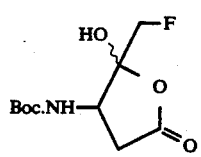 | 85%/36%$^a$ |
| 1h | Boc—TyrOH<br>\\<br>(OBzl) | 2h Boc—TyrCHFCOOBzl<br>\\<br>(OBzl) | 3h Boc—TyrCH$_2$F | 93%/69% |
| 1i | Boc—LeuOH | 2i Boc—LeuCHFCOOBzl | 3i Boc—LeuCH$_2$F | 86%/66% |

TABLE 5-continued $$R\text{—}\underset{O}{C}\text{—}OH \xrightarrow[\text{2) MBFM}]{\text{1) CDI}} R\text{—}\underset{O}{C}\text{—}\underset{F}{CH}\text{—}\underset{O}{C}\text{—}OBzl \xrightarrow{H_2/Pd} R\text{—}\underset{O}{C}\text{—}CH_2F$$

| ENTRY | | | | | | YIELD (2a-j/3a-j) |
|---|---|---|---|---|---|---|
| 1j | p-MeOC$_6$H$_4$CH$_2$COOH (PMPAOH) | 2j | PMPACHFCOOBzl | 3j | PMPACH$_2$F | 92%/83% |

*After chromatography*

TABLE 6

| Compound | $^1$H NMR (ppm) | $^{19}$F NMR (ppm) | IR (cm$^{-1}$) |
|---|---|---|---|
| 2a | 7.35 (5H, s, aromatic); 5.75, 5.1 (1H, 2xd, 47 Hz, CH~F); 5.26 (2H, s, PhCH$_2$); 5.4–5.2 (1H, m, NH); 4.72 (1H, m, CHNH); 1.42 (9H, s, t-Bu); 1.33 (3H, d, 7 Hz, CH$_3$). | −197.6, −198.6 (1F, 2xd, 47 Hz, CH~F). | 3384, 1763, 1741, 1710. |
| 2b | 7.37–7.1 (10H, m, aromatic); 5.7, 5.2 (1H, 2xd, 47 Hz, CH~F); 5.26 (2H, s, CH$_2$O); 5.1–4.75 (2H, m, NH, CHNH); 3.3–2.7 (2H, m, CH$_2$CH); 1.36 (9H, s, t-Bu). | −197.4, −197.7 (1F, 2xd, 47 Hz, CH~F). | 3390, 1715 (br). |
| 2c | 7.37 (5H, s, aromatic); 5.65, 5.2 (1H, 2xd, 47 Hz, CH~F); 5.26 (2H, s, PHCH$_2$); 5.2 (1H, m, NH); 4.38 (1H, m, CHNH); 2.12 (1H, m, CH(CH$_3$)$_2$); 1.43 (9H, s, t-Bu); 1.05–0.95, (CH$_3$)$_2$. | −196.8, −197.8 (1F, 2xd, 47 Hz, CH~F). | 3400, 1766, 1752, 1716. |
| 2d | 7.8–7.2 (m, aromatic); 5.8–5.1 (m, CH~F, PhCH$_2$O); 4.9–4.0 (NH, NH, CHNH, fluorenylCH$_2$O); 3.03 (m, CH$_2$NH), 1.93–1.9–1.3 (m, s, t-Bu, CH$_2$'s). | −197.5, −198.3 (1F, 2xd, 47 Hz, CH~F). | 3336, 2250, 1694 (br), 1560. |
| 2e | Spectra too complicated by impurities to be reported accurately. Mtr residues observed at 6.49, 3.79, 2.65, 2.58, 2.1 ppm ($^1$H) and CH~F residues observed at −197.4, −197.9 ppm ($^{19}$F). Accurate spectra are reported for 3e (see Table 5). | | |
| 2f | 7.35 (5H, s, aromatic); 5.7, 5.2 (1H, 2xm*, CH~F); 5.27 (2H, s, PhCH$_2$); 4.35 1H, m, CHN); 3.46 (2H, m, CH$_2$N); 2.1–1.7 (4H, br m, CH$_2$CH$_2$(ring)); 1.42, 1.35 (9H, 2xs, t-Bu). | −197.6 (dd, CH~F, one isomer, coupled to CHNH and CF~H), −197.9 (same, other isomer). | 3468, 1745, 1719, 1698. |
| 2g | 7.35 (10H, s, aromatic); 5.81, 5.34 (1H, 2xd, 47 Hz, CH~F); 5.57 (1H, m, NH); 5.3–5.1 (4H, m, PhCH$_2$'s); 4.87 (1H, m, CHNH); 3.0 (2H, m, CH$_2$CH), 1.43 (9H, s, t-Bu). | −196.7, 197.8 (1F, 2xd, CH~F). | 3390, 1737. |
| 2h | 7.37 (5H, s, PhCH$_2$); 7.1–6.9 (4H, m, Tyr ring); 5.2 (2H, s, CH$_2$O); 5.8–4.8 (3H, m, CH~F, NH, CHNH); 3.4–2.6 (2H, m, CH$_2$(Tyr)); 1.34 (18H, 2xs, t-Bu's. | −197.9, −197.8 (1F, 2xd, 47 Hz, CH~F). | 3392, 1766, 1740, 1712. |
| 2i | 7.37 (5H, s, aromatic); 5.72, 5.24*, (1H, 2xd, 47 Hz, CH~F); 5.28 (2H, s, PhCH$_2$); 5–4.6 (2H, m, NH, CHNH); 1.8–1.2* (3H, m, CH(CH$_3$)$_2$, CH$_2$CH); 1.43 (9H, s, t-Bu); 0.92 (6H, m, (CH$_3$)$_2$). | −197.5, −198.5 (1F, 2xd, CH~F). | 3388, 1740, 1731, 1713. |
| 2j | 7.35 (5H, s, benzyl Ph); 7.1 (2H, d, 8.6 Hz, 2' CH's); 6.8 (2H, d, 3' CH's); 5.23 (1H, d, 47 Hz, CHF); 5.20 (3H, s, CH$_3$O); 3.87 (2H, d, J$^2$= 3Hz, CH$_2$CO); 3.78 (2H, s, CH$_2$O). | −194.5 (d, 47 Hz). | 1763, 1748, 1735. |

EXAMPLE 15

General Procedure for Fluoromethyl Ketone Synthesis. To a solution of the beta-keto-alpha-fluoroester (Table 5, compound 2a-j) in either toluene, ethyl acetate, or ethanol (0.5 M) is added 10% palladium on activated charcoal (10% by weight of substrate). The mixture is subjected to catalytic hydrogenolysis on a Parr shaker overnight. The mixture is filtered, evaporated (if the reaction solvent is ethanol), diluted with ethyl acetate to 2x volume, washed with saturated aqueous NaHCO$_3$, brine, dried over MgSO$_4$, filtered, and evaporated to dryness.

EXAMPLE 16

Specific Procedure: (3S)-3-tert-butoxycarbonylamino-1-fluoro-5-methyl-2-hexanone. To a solution of Boc-LeuCHFCOOBzl (3.58 g, 9.39 mmol) in ethanol (50 mL) was added 10% palladium on active charcoal (0.36 g). The mixture was subjected to hydrogenolysis on a Parr shaker for 36 hours. The solution was filtered and the solvent was evaporated. The residue was dissolved in ethyl acetate (100 mL), washed with saturated aqueous NaHCO$_3$ (50 mL), brine (50 mL), dried over MgSO$_4$, filtered, and evaporated to give an almost colorless, viscous oil, Boc-LeuCH$_2$F (1.53 g, 66%).

EXAMPLE 17

Alternative Procedure for Fluoromethyl Ketone Synthesis. (3S)-4-tert-butoxycarbonylamino-1-fluoro-3-methyl-2-butanone. To a solution of Boc-L-alanine (13.87 g, 73.36 mmol) in THF (300 mL) was added carbonyl 1,1'diimidazole (11.90 g, 73.36 mmol). The mixture was stirred for 1 hour. During the last 15 minutes of this hour, magnesium benzyl fluoromalonate (18.0 g, 40.35 mmol, 0.55 eq.) was dissolved in THF (70 mL). This solution was added to the imidazolide. The reaction mixture was stirred overnight at room temperature under $N_2$. 1M HCl (70 mL) was added. The mixture was shaken vigorously and allowed to separate. The aqueous layer was extracted with ethyl acetate (150 mL). The organic phases were combined, washed with saturated aqueous $NaHCO_3$ (150 mL), and brine (100 mL), dried over $MgSO_4$, and filtered. With the rotary evaporator bath at <30° C., the solution was concentrated to a volume of −150 mL. This solution was transferred to a Parr bottle. 10% palladium on active charcoal was added. The mixture was subjected to catalytic hydrogenolysis overnight. The solution was filtered, washed with 1M HCl (50 mL), saturated aqueous $NaHCO_3$ (50 mL), and brine (50 mL), dried over $MgSO_4$, filtered, and evaporated to dryness, again with the rotary evaporator bath at ≦30° C. The product, Boc-AlaCH$_2$F, weighed 8.59 g (57% from BocAlaOH).

It was found that best results were obtained by the use of toluene as the extractant/hydrogenolysis solvent, and by limiting the reaction time to 6 hours for the C-acylation process. Using these conditions, optical integrity (at the amino acid residue) was preserved entirely, as evidenced by HPLC of Boc-AlaCH$_2$F on a CHIRALCEL OJ column (DAICEL INDUSTRIES).

EXAMPLES 18–26

Using the general techniques of Examples 15–17 but varying the starting materials among the materials tested as 2a-2j in Table 5 the various products listed as 3a-3j in Table 5 were obtained.

Physical data for fluoromethyl ketones)a-3j are presented in Table 7.

TABLE 7

| Compound | $^1$H NMR (ppm) | $^{19}$F NMR (ppm) | IR (cm$^{-1}$) |
|---|---|---|---|
| 3a | 5.27, 4.80 (2H, d, 47 Hz, CH$_2$F); 5.08 (1H, m, NH); 4.59 (1H, m, CHNH); 1.44 (9H, s, t-Bu); 1.37 (3H, d, 7 Hz, CH$_3$). | −231.8 (1F, t, 47 Hz, CH$_2$F). | 3344, 1742, 1698. |
| 3b$^a$ | 7.34–7.09 (5H, m, aromatic); 5.09, 4.62 (2H, dd, J$^2_{HF}$=47 Hz, J$^4_{HF}$=4Hz, CH$_2$F); 5.02 (1H, m, NH); 4.76 (1H, m, CHNH); 3.24–2.97 (2H, 2xdd*, PHCH$_2$); 1.40 (9H, s, t-Bu). | −230.5 (1F, t, 47 Hz, CH$_2$F). | 3362, 1716 (br). |
| 3c | 5.11, 4.75 (2H, d, 47 Hz, CH$_2$F); 5.05 (1H, m, NH); 4.58 (1H, CHNH); 2.21 (1H, m, CH(CH$_3$)$_2$); 1.45 (9H, s, t-Bu); 1.03, 0.85 (6H, 2xd, 7 Hz, CH$_3$'s). | −230 (1F, t, 47 Hz, CH$_2$F). | 3350, 1716. |
| 3d | 7.9–7.2 (9H, m, aromatic); 5.66 (1H, br, d, NH); 5.2, 4.75 (2H, d, 47 Hz, CH$_2$F); 5.15–4.1 (4H, m*, NH, CHNH, CH$_2$O); 3.1 (2H, m, CH$_2$N); 1.43 (9H, s, t-Bu); 2.1–1.3 (6H, m*, (CH$_2$)$_3$). | −231.3 (1F, t, 47 Hz, CH$_2$F). | 3334, 1702 (br), 1522. |
| 3e | 6.55 (1H, s, aromatic); 6.3 (3H, br, s, NH's (guanidino)); 5.58 (1H, br, d, NH-Boc); 5.22, 4.75 (2H, d, 47 Hz, CH$_2$F); 4.44 (1H, m, CHNH); 3.83 (3H, s, CH$_3$O); 3.23 (2H, m, CH$_2$N); 2.66 (3H, s, CH$_3$); 2.59 (3H, s, CH$_3$); 2.13 (3H, s, CH$_3$); 1.41 (9H, s, t-Bu); 1.8–1.3 (4H, m*, (CH$_2$)$_2$. | −231.4 (1F, t, 47 Hz, CH$_2$F). | 3340, 1694 (br), 1654–1620 (br), 1558. |
| 3f | 5.27, 4.8 (2H, 2xd, 47 Hz, CH$_2$F); 4.58 (1H, m, CHN); 3.5 (2H, m, CH$_2$N); 2.1–1.8 (4H, m, (CH$_2$)$_2$); 1.46, 1.42 (9H, 2xs, t-Bu). | −231.8, −232.4 (1F, 2xt, CH$_2$F) shows up as 2 conformers. | 1740, 1726. |
| 3g | 5.30–4.97 (2H, 2xm, CH$_2$F); 4.5 (2H, br, m, NH, CHNH); 2.90 (2H, 2xdd*, CH$_2$CH); 1.46 (9H, s, t-Bu). After D$_2$O shake, 4.83 (1H, m, one CH$_2$F signal); 4.53 (2H, other CH$_2$F signal, CHND); 2.92 (2H, m, CH$_2$CH); 1.46 (9H, s, t-Bu). | −229 to −233 (br., CH$_2$F). After D$_2$O shake, −230, −232 (2xt*, poor resoln.) After NaHCO$_3$ wash, −228 (t). | 3346, 1714, 1684, 1682 |
| 3h | 6.99 (4H, dd, aromatic); 5.05, 4.58 (2H, dd, J$_{CF}$=47 Hz , CH$_2$F); 5.01 (1H, m, NH); 4.78 (1H, m, CHNH); 3.0 (2H, m, CH$_2$CH); 1.41 (9H, s, t-Bu ether); 1.33 (9H, s, t-BuOOC). | −230.5 (1F, t, 47 Hz, CH$_2$F). | 3340, 1740, 1706, |
| 3i | 5.22, 4.79 (2H, d, 47 Hz, CH$_2$F); 4.95 (1H, m, NH); 4.65 (1H, m*, CHNH); 1.7–1.5 (3H, m*, CH$_2$CH and CHCH$_3$)$_2$; 1.44 (9H, s, t-Bu); 1.01–0.92 (2xd, (CH$_3$)$_2$). | −231.1 (1F, t, 47 Hz, CH$_2$F). | 3340, 1712 (br). |
| 3j | 7.14 (2H, d, 8.5 Hz, para-substituted aromatic); 6.86 (2H, d, 8.5 Hz, para-substituted aromatic); 5.09, 4.61 (2H, d, 48 Hz, CH$_2$F); 3.79 (3H, s, CH$_3$O); 3.77 (2H, m, CH$_2$C=O). | −227.1 (1F, tt, J$^2_{HF}$=48 Hz, J$^4_{HF}$=3.3 Hz | 1732. |

EXAMPLE 27

(3S)-4-amino-1-fluoro-3-butanone hydrochloride. To a solution of Boc-AlaCH$_2$F (7.5 g, 36.5 mmol) in anhydrous ether (60 mL) was added a saturated solution of HCl gas in ether (50 mL). The mixture was stirred vigorously at room temperature. After 45 minutes, the suspension was filtered, and the solids were quickly washed with ether (3×30 mL) and pumped dry overnight, to give 4.10 g (79%) of HCl.AlaCH$_2$F.

TABLE 8-continued

| Example | RCOOH $\xrightarrow[\text{2) immediate H}_2\text{/Pd/EtOAc}]{\text{1) CDI/MBFM (0.6 eq.)}}$ RCH$_2$F | | Yield |
|---|---|---|---|
| 35 | Boc—PheOH | Boc—PheCH$_2$F | 60% |
| 36 | Boc—Asp(OBzl)OH | Boc—AspCH$_2$F | 44% |
| 37 | Fmoc—Lys—OH<br>\|<br>Boc | Fmoc—LysCH$_2$F<br>\|<br>Boc | 26% |
| 38 | Boc—ArgOH<br>\|<br>Mtr | Boc—ArgCH$_2$F<br>\|<br>Mtr | 50%[a] |
| 39 | Boc—ValOH | Boc—ValCH$_2$F | 47%[b] |

Notes:
[a] 2.5 eq. MBFM used;
[b] 2.5 eq. MBFM, 60 hours reaction time in acylation step The quality of the products were in all cases affected by the purity of the magnesium reagent. Strict control of the purity of MBFM was required to ensure that impurities did not surface later. An example of this was observed when benzyl fluoromalonic acid was permitted to react with magnesium ethoxide for longer than 2 or 3 hours, of was allowed to stand in the THF solution for any length of time beyond this. Ethanol produced as the result of reaction between the acid and magnesium ethoxide reacted in ester-exchange manner with MBFM, giving a product contaminated with magnesium ethyl fluoromalonate. When used in the C-acylation step, the result was an inseparable mixture of beta-keto-benzyl ester and beta-keto-ethyl esters. Another potential difficulty was the appearance of fluoromalonic acid (and subsequently its magnesium salt) in some batches of MBFM.

In all cases, however, the optimum quality of MBFM was obtainable simply by maintaining strict pH control during isolation of benzyl fluoromalonic acid, and by precipitating MBFM immediately from its filtered THF

EXAMPLES 40–45

The single amino acid fluoroketones could then be elaborated further as shown in these Examples. (These Examples as well as two previously described elaborations are summarized in Table 9). Deprotection of the alpha-blocking group, followed by mixed anhydride condensation with the appropriate amino acid sequence afforded the appropriate peptide fluoromethyl ketones, which could then be used as protease inhibitors. Of special importance was the preservation of stereochemistry of the group alpha to the fluoromethyl ketone moiety. This was demonstrated to be largely preserved in many cases, as determined by NMR spectra of the peptides. In some cases, however, it was not clear whether splitting of NMR signals was due to tautomeric phenomena or to isomeric mixtures. It was clear, however, that the valine derivative Boc-Ala-Ala-Pro-ValCH$_2$F and Z-Phe-AlaCH$_2$F were one isomer, based on the NMR signals for each. The $^{19}$F NMR signal for Z-Gly-Leu-PheCH$_2$F showed a majority of one product over the other insofar as two triplets in an estimated ratio of 2 5:1 were observed. The $^1$H NMR spectrum of this compound, however, indicated only one species to be present.

It is possible to infer from this data that any stereochemical scrambling of the fluoroketone alpha-carbon may have taken place during deprotection of the alpha-N-Boc group or during coupling, and that such scrambling may be due to such reaction conditions.

TABLE 9

| Example | Starting fluoroketone | Amino acid chain to be added | Peptide fluoroketone product | Enzyme target |
|---|---|---|---|---|
| 29 | Boc—AlaCH$_2$F | Z—PheOH | Z—Phe—AlaCH$_2$F | Cathepsin B, L, S |
| 31 | Boc—PheCH$_2$F | Z—PheOH | Z—Phe—PheCH$_2$F | Cathepsin L |
| 40 | Boc—PheCH$_2$F | Z—Gly—LeuOH | Z—Gly—Leu—PheCH$_2$F | Cathepsin G |
| 43 | Boc—LeuCH$_2$F | Boc—Phe—Gly—LeuOH | Boc—Phe—Gly—Leu—LeuCH$_2$F | Viral protease |
| 41 | Boc—ValCH$_2$F | Boc—Ala—Ala—ProOH | Boc—Ala—Ala—Pro—ValCH$_2$F | H.L. elastase |
| 42 | Boc—ArgCH$_2$F<br>\|<br>Mtr | Z—PheOH | Z—Phe—ArgCH$_2$F.HBr | Cathepsin B, L |

EXAMPLE 40

3-benzyloxycarbonylglycylleucylamino-1-fluoro-4-phenyl-2-butanone. Z-Gly-LeuOH was made by mixed anhydride coupling of Z-GlyOH and LeuOBzl tosylate, followed by NaOH hydrolysis of the benzyl ester. To a solution of Z-Gly-LeuOH (0.223 g, 0.69 mmol) in THF (4 mL) ( at −20° C. was added NMM (76 uL, 0.69 mmol), followed by IBCF (90 uL, 0.69 mmol). After 10 minutes, a precooled solution of PheCH$_2$F hydrochloride (0.15 g, 0.69 mmol) in DMF (1 mL) was added, followed by a second equivalent (76 uL, 0.69 mmol) of NMM. After 30 minutes of stirring, the mixture was quenched with 1M HCl (5 mL), extracted with ethyl acetate (20 mL), washed with saturated aqueous NaHCO$_3$ (6 mL), brine (5 mL), dried over MgSO$_4$, filtered, and evaporated to dryness. The residue was crystallized from ether/hexane to give 0.18 g (54%) of Z-Gly-Leu-PheCH$_2$F.

$^1$H NMR (CDCl$_3$) 7.4–7.1 (11H, m, aromatic, NH); 6.65 (1H, d, NH); 5.63 (1H, m, NH); 5.10 (2H, s, CH$_2$O); 5.05, 4.61 (2H, dd, 47,6 Hz, CH$_2$F); 4.92 (1H, m*, CHCH$_2$Ph); 4.43 (1H, m, CHNH(Leu)); 3.8 (2H, d, CH$_2$NH); 3.3–2.8 (2H, 2xdd, PhCH$_2$CHO; 1.7–1.1 (3H, m, CH$_2$CH(Leu), CH(CH$_3$)$_2$); 0.87,0.84 (6H, m, (CH$_3$)$_2$) $^{19}$F NMR (CDCl$_3$): -230.5 (1F. t, 47 Hz, CH$_2$F). IR (thin film): 3298 (br); 1740,1648.

EXAMPLE 41

(3S)-3-tert-butoxycarbonylalanylalanylprolyl-amino-1-fluoro-4-methyl-2-pentanone. To a solution of Boc-ValCH$_2$F (0.48 g, 2.06 mmol) in ether (10 mL) was added a saturated solution of HCl in ether (25 mL). The mixture was stirred for 30 minutes at room temperature. The solvent was evaporated under reduced pressure at room temperature. The residue was quickly triturated with ether (2×30 mL) and then was pumped dry, giving 0.24 g of ValCH$_2$F hydrochloride. Boc-Ala-Ala-ProOH (Enzyme Systems Products, 0.503 g, 1.41 mmol) was dissolved in THF (5 mL) and was cooled to −20° C. NMM (0.155 mL, 1.41 mmol) was added, followed by IBCF (0.183 mL, 1.41 mmol). After 5 minutes, this mixture was charged with a solution of ValCH$_2$F $^1$H NMR (CDCl$_3$/DMSO-d$^6$): 9.6 (3H, br.s, NH$_3$+); 5.39, 4.92 (2H, d, 47 Hz, CH$_2$F); 4.23 (1H, m, CHC=O); 1.46 (3H, d, 7 Hz, CH$_3$). $^{19}$F NMR (CDCl$_3$/DMSO-d$^6$): -228.1 (1F, t, 47 Hz, CH$_2$F).

EXAMPLE 28

(3S)-4-amino-1-fluoro-3-butanone p-toluenesulfonate. To a solution of Boc-AlaCH$_2$F (2.00 g, 9.75 mmol) in diisopropyl ether (10 mL) was added a solution of azeotropically dried anhydrous p-toluenesulfonic acid (4.15 g, 24.36 mmol) in diisopropyl ether (50 ml). The mixture was stirred vigorously at room temperature. After 3 hours, the suspension was filtered, and the solids were washed with diisopropyl ether (3×30 mL) and pumped dry overnight, to give 2.12 g (78%) of p-TsOH- .AlaCH$_2$F. 682

$^1$H NMR (CDCl$_3$/DMSO-d$^6$): 8.3 (3H, br.s, NH$_3$+); 7.75 (2H, d, 6 Hz, aromatic); 7.2 (2H, d, 6 Hz, aromatic); 5.45, 4.98 (2H, d, 47 Hz, CH2F); 4.35 (1H, m, CHC=O); 2.34 (3H, s, CH$_3$-Ar); 1.46 (3H, d, 7 Hz, CH$_3$). $^{19}$F NMR (CDCl$_3$/DMSO-d$^6$): -228.8 (1F, t, 47 Hz, CH$_2$F).

EXAMPLE 29

(3S)-3-(benzyloxycarbonylphenylalanylamino)-1-fluoro-2-butanone Z-phenylalanine (2.29 g, 7.65 mmol) was 5 dissolved in THF (35 mL). The solution was cooled to −10° C. (methanol/ice bath). N-methylmorpholine (NMM; 0.84 mL, 7.65 mmol) was added, followed by isobutyl chloroformate (IBCF; 0.991 mL, 7.65 mmol), added over 3 minutes. With stirring, in a separate flask cooled to −15° C., p-TsOH.AlaCH$_2$F (2.11 g, 7.65 mmol) was dissolved in DMF (7 mL). This solution was added to the mixed anhydride. NMM (0.84 mL, 7.65 mmol) was added. The reaction mixture was stirred for 45 minutes at between −10° C. and −5° C. 1M HCl (50 mL) was added. The mixture was extracted with ethyl acetate (2×50 mL). The organic phases were combined, washed with saturated aqueous NaHCO$_3$ (2×50 mL), brine (50 mL), dried over MgSO$_4$, filtered, and evaporated to dryness. The crude solid was precipitated from 7:1 hexane/CH$_2$Cl$_2$ (100 mL). After filtration, the solid was recrystallized from isiporpanol, yielding pure Z-Phe-AlaCH$_2$F (2.13 g, 72% from p-TsOH.AlaCH$_2$F).

$^1$H NMR (CDCl$_3$): 7.3-7.1 (10H, m, aromatics); 6.72 (1H, br.d, NH); 5.51 (1H, br.d, NH); 5.11, 4.65 (2H, d, 47 Hz, CH$_2$F); 5.1 (2H, s, CH$_2$O); 4.74 (1H, m*, CHCH$_3$); 4.43 (iH, m, CHCH$_2$Ph); 3.06 (2H, d, 6 Hz, CH$_2$Ph); 1.27 (3H, d, 7 Hz, CH$_3$). $^{19}$F NMR (CDCl$_3$): -232.5 (1F, t, 47 Hz, CH$_2$F). $^{13}$C NMR (CDCl$_3$): 204.61 (dd, J$^2_{cf}$=19 Hz, ketone C=O); 170.7 (amide C=O); 155.9 (urethane C=O); 136.05 (ipso C); 135.99 (ipso C); 129.2, 128.7, 128.5, 128.8 (o,m CH's); 128.2, 127.1 (p CH's); 87 (d, J$^1_{cf}$=185 Hz, CH$_2$F); 67.1 (CH$_2$O); 56.8 (CHCH$_2$Ph); 51.0 (CHCH$_3$); 39.4 (CH$_2$Ph); 16.5 (CH$_3$). IR (thin film): 3350,1750,1710,1660. Analysis: C,65.3%, H,6.0%, F,4.9%, N,7.3% (calculated), C,65.3%, H,6.01%, F,4.90%, N,7.25%(found). [alpha]$_{Hg}^{20}$ = −21.6±0.3° (c=1, CH$_3$OH) M.p. 143°-146° C.

EXAMPLE 30

3-amino-1-fluoro-4-phenyl-2-butanone. To a solution of Boc-PheCH2F (0.75 g, 2.67 mmol) in anhydrous ether (5 mL) was added a saturated solution of HCl in ether (30 mL). The mixture was stirred vigorously at room temperature for 45 minutes. The suspension was filtered, washed with ether (10 mL), and pumped dry, to give a white solid (0.31 g, 54%). This material was immediately used in the next step.

EXAMPLE 31

3-benzyloxycarbonylphenylalanylamino-1-fluoro-4-phenyl-2-butanone. To a solution of Z-PheOH (0.207 g, 0.69 mmol) in THF (4 mL), cooled to −20° C., were added NMM (76 uL, 0.69 mmol) and IBCF (90 uL, 0.69 mmol). After 10 minutes, a chilled (−10° C.) solution of PheCH2F hydrochloride (0.15 g, 0.69 mmol) in DMF (1 mL) was added, followed by NMM (76 uL, 0.69 mmol). The mixture was stirred for 30 minutes. 1M HCl (5 mL) was added. The solution was extracted with ethyl acetate (30 mL), washed with saturated aqueous NaHCO$_3$ (6 mL), brine (4 mL), dried over MgSO$_4$, filtered, and evaporated to dryness. The residue was crystallized from ethyl acetate/hexane, yielding 0.22 (53%) of Z-Phe-PheCH$_2$F.

$^1$H NMR (CDCl$_3$): 7.33-7.22 (15H, m, aromatic); 6.3 (1H, m, NH); 5.02 (2H, s, CH$_2$O); 5.02-4.9,4.6,4.5 (4H, m*, CHNH, CH$_2$F, CHNH0; 3.0 (2H, m, CHCH$_2$). $^{19}$F NMR (CDCl$_3$): -230.3 (1F, t, 47 Hz, CH$_2$F).

EXAMPLE 32

A modified procedure was next developed to incorporate the fact that the reagent MBFM has the elements of two "—CH$_2$F" moieties available for reaction. It was found that the C-acylation reaction could be performed using less than 1 mole equivalent of MBFM with respect to the carboxylic acid and to CDI; in fact 0.6 equivalents was the quantity used in the modified procedure. That the yields did not suffer is evidenced by comparing entry 2j in Table 5 above with Table 8 below.

EXAMPLE 33

An additional modification was then incorporated. The beta-keto-alpha-fluoresters 2a-j tended to decompose on standing over a period of days, either neat, or in solution in CDC13. Decomposition also occurred to some extent if the neat beta-ketoesters were heated at 40°-45° C.; it is also likely that some racemization of the amino acid residues (entries 2a-i) could occur under such conditions. Since 2a-j were designed to be intermediates to be used immediately, these compounds were subjected to workup in the usual manner, but instead of the solutions being concentrated to dryness (for example, on a rotary evaporator at 40°-45° C.), they were reduced in volume at room temperature to approximately 0.3M in ethyl acetate/ THF, the workup solvents. The solutions were then hydrogenolyzed directly in the presence of palladium catalyst, and were worked up in the usual manner. Small samples of the beta-ketoesters were stripped to dryness at room temperature for the purpose of analytical data collection.

EXAMPLES 34–39

The above modifications (0.6 equivalents of MBFM, and immediate hydrogenolysis of the washed and dried beta-keto-alpha-fluorester solutions) were successfully employed in the following examples, illustrated in Table 8.

TABLE 8

| Example | RCOOH | 1) CDI/MBFM (0.6 eq.) 2) immediate H$_2$/Pd/EtOAc → RCH$_2$F | Yield |
|---|---|---|---|
| 34 | Boc—AlaOH | Boc—AlaCH$_2$F | 57% | hydrochloride (0.24 g, 1.41 mmol) in DMF (2 mL). A second equivalent of NMM (0.155 mL, 1.41 mmol) was added. The mixture was stirred at −15° C. for 15 minutes. 1 molar HCl (15 mL) was added. The product was extracted with ethyl acetate (2×15 mL). The combined extracts were washed with saturated aqueous NaHCO$_3$ (15 mL), brine (15 mL), dried over MgSO$_4$, filtered, and evaporated to dryness The residue was slowly crystallized at −20° C. from CH$_2$Cl$_2$/hexane, giving 0.47 g (47% from Boc-ValCH$_2$F of Boc-Ala-Ala-Pro-ValCH$_2$F.

$^1$H NMR (CDCl$_3$) 7.55-7.3 (2H, m*, NH,NH); 5.2 (1H, m*, NH(Boc)); 5.25,4.78 (2H, d, 47 Hz, CH$_2$F); 5.0-4.65 (3H, m*, CHNH's) 4.37 (1H, m, CHNHO: 3.70 (2H, m, CH$_2$N); 2.4-1.9 (5H, CH$_2$Ch$_2$CHN,CH(CH$_3$($_2$); 1.45 (9H, s, t-Bu); 1.35 (3H, d, 7 Hz, CH$_3$(Ala)); 1.3 (3H, d, 7 Hz, CH$_3$Ala)); 1.3 (3H, d, 7 Hz, CH$_3$(Ala)); 1.04-0.82 (6H, 2xd, 7 Hz, (CH$_3$)$_2$). $^{19}$F NMR (CDCl$_3$): -229.9 )1F, t, 47 Hz, CH$_2$F). 1R (thin film) 3303 (br); 1730,1634(br).

EXAMPLE 42

3-benzyloxycarbonylphenylalanylamino-1-fluoro-6-quanidino-2-hexanone. 3-tert-butoxycarbonylamino-1-fluoro-6-(4-methoxy-2,3,6-trimethylphenyl -sulfonyl)-guanidino-2-hexanone (Boc-Arg(Mtr)CH$_2$F; 0.75 g, 1.49 mmol) was treated with a 30% solution of HBr in acetic acid for 3 hours at room temperature. The orange oil was then added, with vigorous stirring, to ether (200 mL), stirred for 5 minutes more, and then filtered, the solids being washed with 2×20 mL portions of fresh ether. The solid was immediately pumped dry overnight.

To a solution of Z-PheOH (0.409 g, 1.367 mmol) in THF (7 mL), cooled in a methanol/ice bath, were added NMM (0.15 mL, 1.37 mmol), followed by IBCF (0.177 g, 1.367 mmol). The solid (HBr)$_2$.ArgCH$_2$F previously made was dissolved in DMF (5 mL) and was added to the reaction mixture. NMM (0.15 mL, 1.37 mmol) was added. The mixture was stirred for 45 minutes, whereupon the solvents were removed under high vacuum. The residue was dissolved in n-butanol (70 mL). The solution was washed with 1M HCl (25 mL), saturated aqueous NaHCO$_3$ (25 mL), and brine (25 mL). The organic layer was filtered through a glass wool plug and the solvent was evaporated. The residue was purified by chromatography on 60-230 mesh silica using 20% CH$_3$OH/CH$_2$Cl$_2$ as eluent. After evaporation of the product-containing fractions, the solid product was precipitated from CH$_2$Cl$_2$/ether, giving 0.32 g (39% from Boc-Arg(Mtr)CH$_2$F) of Z-Phe-ArgCH$_2$F.HBr. $^1$H NMR (CDCl$_3$) 8.7,7.75 (m, NH's); 7.29 (aromatics=NH's); 5.26,4.8* (CH$_2$F); 4.96 (2H, s, CH$_2$O); 4.5-4.0 (CHNH's); 3.1 (2H, m, CH$_2$Ph); 2-1.3 (CH$_2$CH$_2$-guanidino). $^{19}$F NMR (CDCl$_3$): −227.51, −228.05 (2xt, 47 Hz, CH$_2$F; either diastereomers at Arg residue or hydrogen bonding effects).

EXAMPLE 43

3-tert-butoxycarbonylphenylalanylqlycylleucyl-amino-1-fluor-5-methyl-2-hexanone. To a solution of Boc-LeuCH$_2$F (1.53 g, 6.19 mmol) in ether (30 mL) was added a saturated solution of HCl in ether (20 mL). The mixture was stirred vigorously; a precipitate formed within 15 minutes. After 1 hour, the mixture was filtered, the solids were washed with ether (2×30 mL) and were then pumped dry overniqht: a second crop was obtained from the filtrate, giving 0.60 g (54%) of LeuCH$_2$F hydrochloride. Boc-Phe-Gly-LeuOH (synthesized in several steps via mixed anhydride coupling of the appropriate amino acid benzyl esters and subsequent hydrogenolyses, 0.762 g, 1.69 mmol) was dissolved in THF (10 mL), and was cooled to −20° C. NMM (0.186 mL, 1.69 mmol) was added, followed by IBCF (0.219 mL, 1.69 mmol). After 5 minutes, HCl.LeuCH$_2$F (0.31 g, 1.69 mmol) was dissolved in DMF (2 mL), to which solution was added NMM (0.186 mL, 1.69 mmol). This mixture was swirled for approximately 15 seconds and was added to the mixed anhydride solution. After 45 minutes, the reaction was quenched with 1M HCl (20 mL), extracted with ethyl acetate (2×30 mL), the combined organics were washed with saturated aqueous NaHCO$_3$ (30 mL), brine (20 mL), dried over MgSO$_4$, filtered, and evaporated. The thick oil was then dissolved in 1:1 ether/CH$_2$Cl$_2$ (20 mL), and hexane (50 mL) was added. After one day, the evaporated to dryness, yielding 0.14 g of Boc-Phe-Gly-Leu-LeuCH$_2$F.

$^1$H NMR (CDCl$_3$) 7.7-7.4 (3H, m*, peptide NH's); 7 23 (5H, m, aromatic); 5.49 (1H, br.d, NH-Boc); 5.36,4.89 (2H, dd, J$_{cf}$=47 Hz, CH$_2$F); 4.8-4.2 (3H, m*, CHNH (Phe, Leu), CHCOCH$_2$F); 3.95 (2H, m, CH$_2$NH); 3.3-2.8 (2H, 2xdd, CH$_2$Ph); 1.65 (6H, 2xCH$_2$CH(CH$_3$)$_2$); 1.37 (9H, s, t-Bu); 0.91 (12H, 2x(CH$_3$)$_2$) $^{19}$F NMR (CDCl$_3$): -232 1 (1F, t, CH$_2$F) IR (thin film) 3292,1750–1640 (br).

The above results reflect the versatility of the method and its tolerance of functionality. Worth noting is the aspartic acid entry (1g), in which the liberated beta-carboxylic acid cyclized on the fluoromethyl ketone moiety to give the hydroxylactone form. This is apparently a pH-dependent cyclization, as determined by NMR.

In summary, a new method for the introduction of the —CH$_2$F function has been presented, one which requires mild conditions not usually associated with other methods of fluoromethylation. Yields are generally good to excellent, with the products in most cases not requiring chromatographic purification. The products thus obtained could be converted to peptide fluoromethyl ketones, of potential use as enzyme inhibitors.

What is claimed is:

1. A method for forming a fluoromethyl ketone from a carboxylic acid which comprises the steps of
   a. converting the carboxylic acid to give the corresponding imidazolide,
   b. reacting the imidazolide with a magnesium fluoromalonate of the formula

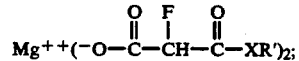

wherein
   X is —O— or —S—, and
   R' is an a hydrogenatively cleavable group
      to yield the corresponding beta-keto-alpha-fluoro-ester of the carboxylic acid, and
   c. hydrogenating the beta-keto-alpha-fluoroester of the carboxylic acid thereby causing its decarboxylation and formation of the fluoromethyl ketone.

2. The method of claim 1 wherein in step c. the hydrogenating is carried out using hydrogen gas and a hydrogenation catalyst.

3. The method of claim 2 wherein in step b. the magnesium fluoromalonate is such that X is —O— and R' is selected from the group consisting of benzyl and substituted benzyl.
4. The method of claim 2 wherein in step b. the magnesium fluoromalonate has the formula
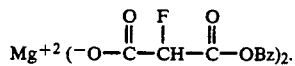
5. The method of claim 2 wherein in step b. the magnesium fluoromalonate has the formula
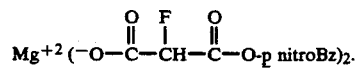
* * * * *

UNITED STATES PATENT AND TRADEMARK OFFICE
CERTIFICATE OF CORRECTION

Page 1 of 4

PATENT NO. : 5,210,272
DATED : May 11, 1993
INVENTOR(S) : James T. Palmer

It is certified that error appears in the above-identified patent and that said Letters Patent is hereby corrected as shown below:

In column 1, line 36, change "welch" to --Welch--.

In column 3, line 58, change "Of" to --of--.

In column 8, line 15, change "EXAMPLES" to --EXAMPLE 1--.

In column 8, line 41, after "(CDCl$_3$)" insert --:--.

In column 9, line 7, after "(CDCl$_3$)" insert --:--.

In column 9, line 9, after "(CDCL$_3$)" insert --:--.

In column 9, line 24, insert a period at the end of the line.

In column 13, line 64, change "$\leq$" to --$\leq$--.

In column 14, line 11, change "ketones)a-3j" to --ketones 3a-3j--.

In column 15, line 16, delete "682".

In column 15, line 19, change "CH2F)" to --CH$_2$F)--.

UNITED STATES PATENT AND TRADEMARK OFFICE
CERTIFICATE OF CORRECTION

Page 2 of 4

PATENT NO. : 5,210,272
DATED : May 11, 1993
INVENTOR(S) : James T. Palmer

It is certified that error appears in the above-identified patent and that said Letters Patent is hereby corrected as shown below:

In column 15, line 26, place a period after the word "butanone".

In column 15, line 62, please center in the column the phrase "EXAMPLE 30".

In column 15, line 64, change "Boc-PheCH2F" to --Boc-PheCH$_2$F--.

In column 16, line 10, change "PheCH2F" to --PheCH$_2$F--.

In column 16, line 40, change "CDCl3" to --CDCl$_3$--.

In column 17, line 50, after "THF" add the words --solution with hexane.--.

In column 18, line 5, change "2 5:1" to --2.5:1--.

In column 18, line 33, change "(at" to --at--.

In column 18, line 50, place a period at the end of the line.

UNITED STATES PATENT AND TRADEMARK OFFICE
CERTIFICATE OF CORRECTION

Page 3 of 4

PATENT NO. : 5,210,272
DATED : May 11, 1993
INVENTOR(S) : James T. Palmer

It is certified that error appears in the above-identified patent and that said Letters Patent is hereby corrected as shown below:

In the original Letters Patent, please note that the page comprising columns 17 and 18 is improperly printed prior to the page comprising columns 15 and 16.

In column 19, line 19, change ")1F," to --(1F,-- and change "(thin film)" to --(thin film):--.

In column 19, line 52, change "($CDCl_3$)" to --($CDCl_3$):--.

In column 20, line 18, after the word "day," add the words --the supernatant was decanted from the impure product and was--.

In column 20, line 19, delete the word "the".

In column 20, line 21, change "($CDCl_3$)" to --($CDCl_3$):--.

UNITED STATES PATENT AND TRADEMARK OFFICE
CERTIFICATE OF CORRECTION

PATENT NO. : 5,210,272
DATED : May 11, 1993
INVENTOR(S) : James T. Palmer

It is certified that error appears in the above-identified patent and that said Letters Patent is hereby corrected as shown below:

In column 20, line 26, change "$2x(CH_3)_2$)" to --$2x(CH_3)_2$):--.

In column 20, line 27, change "(thin film)" to --(thin film):--.

In column 20, lines 64-65, change "hydrogenating" to --hydrogenation--.

Signed and Sealed this

Thirteenth Day of December, 1994

Attest:

BRUCE LEHMAN

Attesting Officer         Commissioner of Patents and Trademarks